(12) United States Patent
Maslowski

(10) Patent No.: US 8,765,121 B2
(45) Date of Patent: Jul. 1, 2014

(54) TREATMENT OF VOCAL CORDS WITH AUTOLOGOUS DERMAL FIBROBLAST FORMULATION

(75) Inventor: John Maslowski, Pottstown, PA (US)

(73) Assignee: Fibrocell Technologies, Inc., Exton, PA (US)

( * ) Notice: Subject to any disclaimer, the term of this patent is extended or adjusted under 35 U.S.C. 154(b) by 0 days.

(21) Appl. No.: 13/879,606

(22) PCT Filed: Oct. 14, 2011

(86) PCT No.: PCT/US2011/056303
§ 371 (c)(1),
(2), (4) Date: Apr. 15, 2013

(87) PCT Pub. No.: WO2012/051505
PCT Pub. Date: Apr. 19, 2012

(65) Prior Publication Data
US 2013/0224160 A1    Aug. 29, 2013

Related U.S. Application Data

(60) Provisional application No. 61/393,247, filed on Oct. 14, 2010.

(51) Int. Cl.
*A01N 63/00* (2006.01)

(52) U.S. Cl.
USPC .......................................... 424/93.7; 128/898

(58) Field of Classification Search
USPC .......................................... 424/93.7; 128/898
See application file for complete search history.

(56) References Cited

U.S. PATENT DOCUMENTS

| | | |
|---|---|---|
| 4,524,065 A | 6/1985 | Pinnell |
| 4,772,557 A | 9/1988 | Eisen |
| 6,110,459 A | 8/2000 | Mickle |
| 6,733,530 B1 | 5/2004 | Lam |
| 7,115,274 B2 | 10/2006 | Keller |
| 7,767,452 B2 | 8/2010 | Kleinsek |
| 7,799,325 B2 | 9/2010 | Kleinsek |
| 8,529,883 B2 * | 9/2013 | Maslowski ............... 424/93.1 |
| 2007/0154462 A1 * | 7/2007 | Kleinsek ............... 424/93.7 |
| 2008/0152628 A1 | 6/2008 | Kleinsek |
| 2009/0123503 A1 * | 5/2009 | Naughton et al. ........... 424/401 |
| 2010/0233138 A1 * | 9/2010 | Payne et al. ............... 424/93.7 |
| 2010/0291045 A1 * | 11/2010 | Jia et al. ............... 424/93.7 |
| 2011/0110898 A1 | 5/2011 | Kleinsek |

FOREIGN PATENT DOCUMENTS

| | | |
|---|---|---|
| WO | 9836704 | 8/1998 |
| WO | 2008002064 | 1/2008 |
| WO | 2008027984 | 3/2008 |

OTHER PUBLICATIONS

Ghahary, et al., "Collagenase production is lower in post-burn hypertrophic scar fibroblasts than in normal fibroblasts and is reduced by insulin-like growth factor-1", J. Invest Dermal., 106(3):46-81 (1996).
Adams and Watt, "Expression of beta 1, beta 3, beta 4, and beta 5 integrins by human epidermal keratinocytes and non-differentiating keratinocytes", J Cell Biol., 115(3):829-41 (1991).
Benninger, et al., "Vocal fold scarring: current concepts and management", Otolaryngol Head Neck Surg., 115:474-82 (1996).
Berke, et al., "Vocal cord augmentation with cultured autologous fibroblasts", Bull Exp Biol Med., 130(8):790-2 (2000).
Boss, et al., "Autologous cultured fibroblasts: a protein repair system", Ann Plast Surg., 44:536-42 (2000).
Byrne, et al., "Producing primate embryonic stem cells by somatic cell nuclear transfer", Nature, 450(7169):497-502 (2007).
Cedervall, et. al., "Injection of embryonic stem cells into scarred rabbit vocal folds enhances healing and improves viscoelasticity: short-term results", Laryngoscope , 117:2075-81 (2007).
Chhetri, et al., "Lamina propria replacement therapy with cultured autologous fibroblasts for vocal fold scars", Otolaryngol Head Neck Surg.,131:864-70 (2004).
Chhetri and Burke, "Injection of cultured autologous fibroblasts for human vocal fold scars", Laryngoscope, 121(4):785-92 doi:10.1002 (2011).
Cowan, et al., "Nuclear reprogramming of somatic cells after fusion with human embryonic stem cells", Science, 309(5739):1369-73 (2005).
Duke, et al., "Fascia augmentation of the vocal fold: graft yield in the canine and preliminary clinical experience", Laryngoscope,111:759-64 (2011).
Gray, et al., "Vocal fold proteoglycans and their influence on biomechanics", Laryngoscope, 109:845-54 (1999).
Hartnick, et al., "Development and maturation of the pediatric human vocal fold lamina propria", Laryngoscope, 115:4-15 (2005).
Hayflick and Moorhead, "The serial cultivation of human diploid cell strains", Exp Cell Res., 25:585-621 (1961).
Hirano, "Current treatment of vocal fold scarring", Curr Opin Otolaryngol Head Neck Surg. 13(3):143-7 (2005).
Hirano, et al., "Histologic characterization of human scarred vocal folds", J Voice 23(4):399-407 (2009).
Hochedlinger, et al., "Epigenetic reprogramming and induced pluripotency", Development, 136(4):509-23 (2009).
Hsiung, et al., "Fat augmentation for glottic insufficiency", Laryngoscope, 110:1026-33 (2000).
Jacobson, et al., "The Voice Handicap Index (VHI)", Am J Speech Lang Pathol.,6:66-70 (1997).
Kanawaty, et al., "Genomic analysis of induced pluripotent stem (iPS) cells: routes to reprogramming", Bioessays.,31(2):134-8 (2009).

(Continued)

*Primary Examiner* — Ralph Gitomer

(74) *Attorney, Agent, or Firm* — Pepper Hamilton, LLP

(57) ABSTRACT

Dosage units consist of an autologous cell therapy product composed of fibroblasts grown for each individual to be treated for augmentation or regeneration of vocal cords. The suspension of autologous fibroblasts, grown from a biopsy of each individual's own buccal mucosa or skin using current good manufacturing practices (CGMP) and standard tissue culture procedures, is supplied in vials containing cryopreserved fibroblasts or precursors thereof, having a purity of at least 98% fibroblasts and a viability of at least 85%, for administration of from one to six mL, preferably two mL administered three times approximately three to six weeks apart, of cells at a concentration of from $1.0\text{-}2.0\times10^7$ cells/mL.

9 Claims, 5 Drawing Sheets

(56) References Cited

OTHER PUBLICATIONS

Kanemaru, et al., "Regeneration of the vocal fold using autologous mesenchymal stem cells", Ann Otol Rhinol Laryngol.,112:915-20 (2003).

Krishna, et al., "Primed fibroblasts and exogenous decorin: potential treatments for subacute vocal fold scar", Otolaryngol Head Neck Surg.,135:937-45 (2006).

Neuenschwander, et al., "Management of vocal fold scar with autologous fat implantation: perceptual results", J Voice, 15:295-304 (2001).

Rosen, "Vocal fold scar: evaluation and treatment", Otolaryngol Clin North Am., 33:1081-6 (2000).

Sparman, et al., "Epigenetic reprogramming by somatic cell nuclear transfer in primates", Stem Cells, 27(6):1255-64 (2009).

Takahashi, et al., "Induction of pluripotent stem cells from adult human fibroblasts by defined factors", Cell, 131(5):861-72 (2007).

Thibeault, et al., "A method for identification of vocal fold lamina propria fibroblasts in culture", Otolaryngol Head Neck Surg., 139(6):816-22 (2008).

Watson, et al., "Autologous fibroblasts for treatment of facial rhytids and dermal depressions. A pilot study", Arch Facial Plast Surg., 1:165-70 (1999).

* cited by examiner

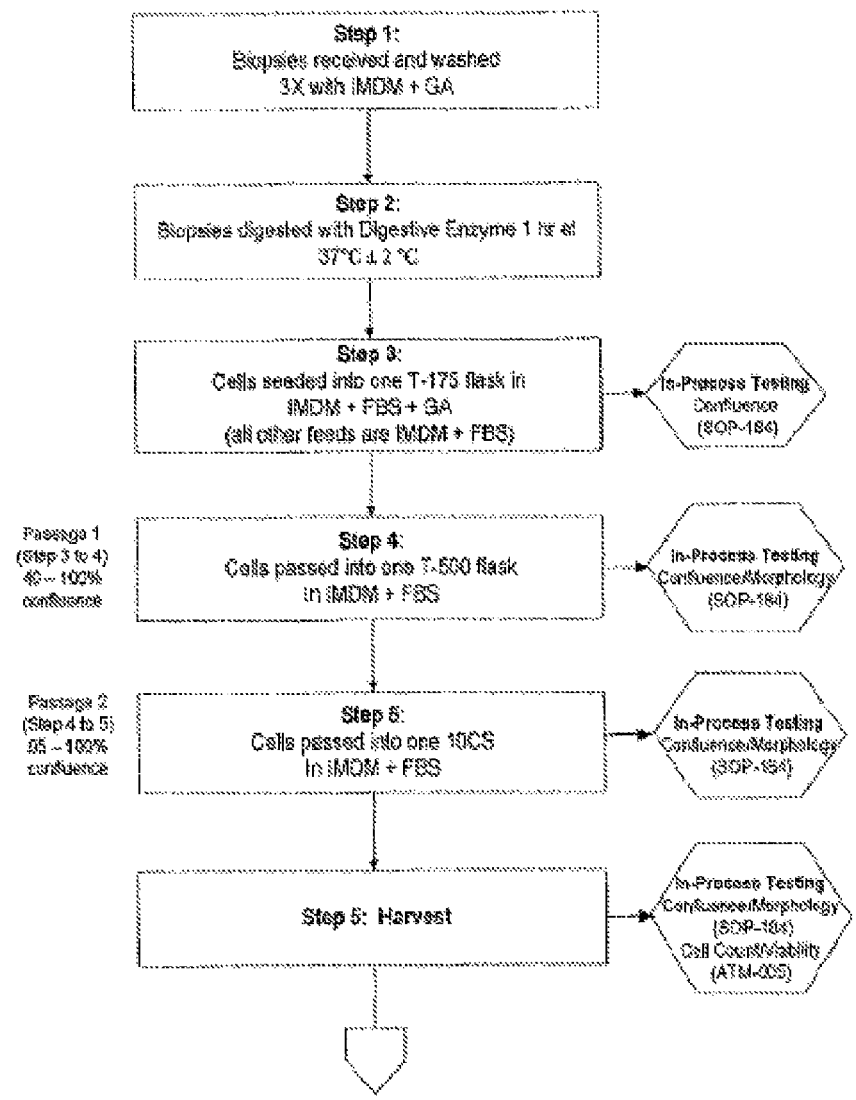

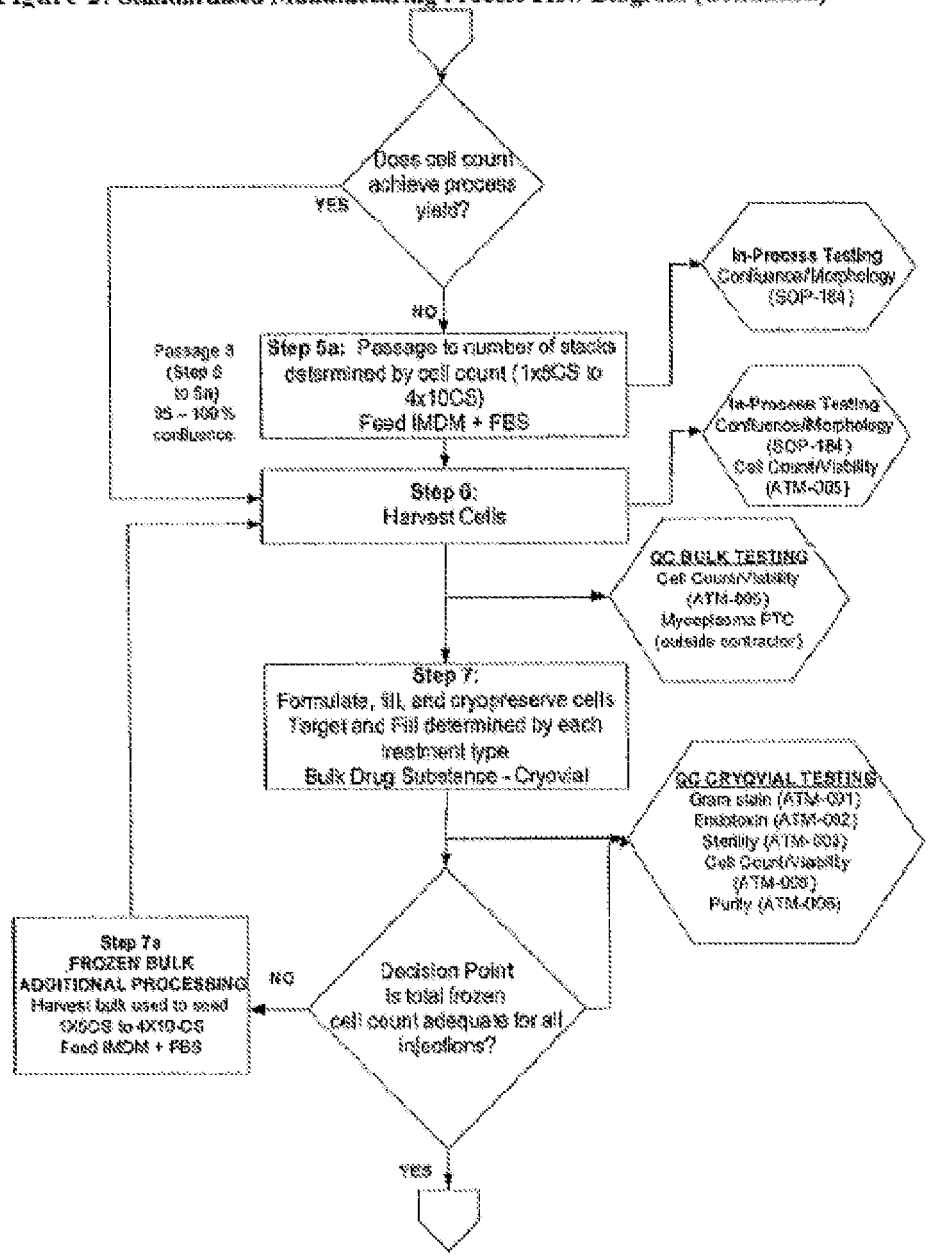
Figure 2: Standardized Manufacturing Process Flow Diagram (Continued)

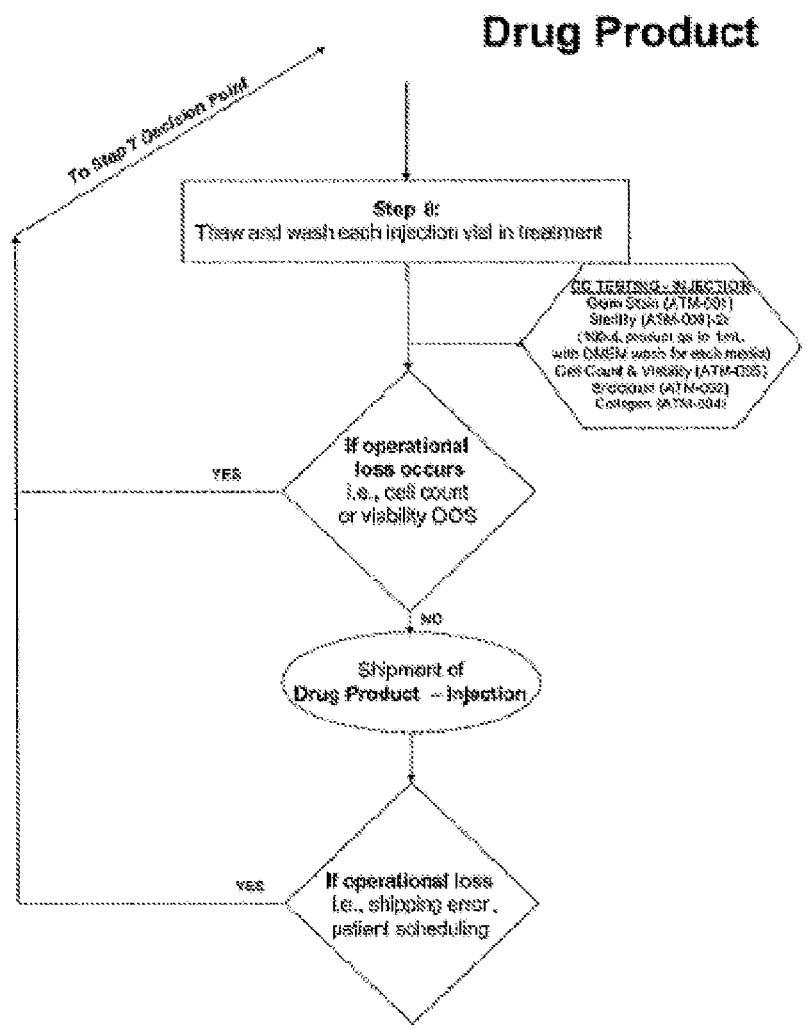
Figure 2: Standardized Manufacturing Process Flow Diagram (Continued)

TREATMENT OF VOCAL CORDS WITH AUTOLOGOUS DERMAL FIBROBLAST FORMULATION

CROSS REFERENCE TO RELATED APPLICATIONS

This application is a national phase filing under 35 U.S.C. §371 of International Application No. PCT/US2011/056303, filed in the United States Receiving Office for the Patent Cooperation Treaty on Oct. 14, 2011, which claims the benefit of and priority to U. S. Provisional Application No. 61/393,247, filed on Oct. 14, 2010, the disclosures of which are herein incorporated by reference in their entirety.

FIELD OF THE INVENTION

This relates to treatment of vocal fold scarring and vocal cord augmentation using isolated, prepared autologous dermal fibroblasts for injection in human subjects.

BACKGROUND OF THE INVENTION

The vocal folds of the human larynx are highly specialized structures that are capable of self-sustained oscillation for production of sound for speech, communication, and singing. The vocal folds are divided anatomically into three tissue layers (Hirano M. *Otologia (Fukuoka)* 1975; 21:239-442). The superficial layer is the vocal fold epithelium, followed by the middle lamina propria layer, and the deep muscular layer (FIG. 1). The epithelial layer is very thin compared to the other layers and acts biomechanically as a functional unit with the lamina propria layer and thus these two layers are combined and called the "cover" layer in biomechanical studies of the vocal fold. The lamina propria layer is an amorphous, paucicellular layer composed mostly of fibroblasts, macrophages and extracellular matrix molecules (Gray et al. *Laryngoscope* 1999; 109:845-54). This layer provides the appropriate viscoelasticity (mucosal pliability) for normal oscillation of the vocal folds during phonation which can be appreciated clinically as mucosal waves on the vocal fold surface upon videostroboscopic examination of the larynx (Hirano et al. *J Voice* 2009; 23(4):399-407). Vocal fold scarring is a pathologic condition that results from loss of the lamina propria layer and leads to glottic insufficiency and diminished or absent mucosal waves on the vocal fold surface, and is a common clinical problem resulting in dysphonia. Treatment of lamina propria loss is of special interest because there is currently no effective replacement therapy.

The most frequent etiology for vocal fold lamina propria loss is surgery on the vocal fold for benign and malignant disorders. Other causes include a variety of traumatic, neoplastic, iatrogenic, inflammatory, and idiopathic disorders (Rosen *Otolaryngol Clin North Am* 2000; 33:1081-6). The resulting voice is often rough and breathy, of poor quality, and perceived by patients as a severe communication handicap. Histologically, lamina propria loss after iatrogenic vocal fold injury occurs as the layer is replaced with dense and disorganized collagen deposits (Hirano *Curr Opin Otolaryngol Head Neck Surg.* 2005 June; 13(3):143-7). This increased fibrosis is referred to clinically as vocal fold scar.

Vocal fold scar is a challenging problem for the otolaryngologist because effective therapy for this condition is currently lacking and rehabilitation of patients is difficult. Management of vocal fold scars with autologous fat implantation and autologous fascia augmentation has been reported but treatment results have been less than satisfactory (Benninger et al. *Otolaryngol Head Neck Surg* 1996; 115:474-82; Neuenschwander et al. *J Voice* 2001; 15:295-304; Duke et al. *Laryngoscope* 2001; 111:759-64). This is because currently no biomaterial exists that matches the native viscoelastic properties of this layer.

There are currently two potential therapeutic modalities for vocal fold scars: (a) Injection of biomaterials into the lamina propria compartment, and (b) cellular based therapy (Hsiung et al. *Laryngoscope* 2000; 110:1026-33; Chhetri et al. *Otolaryngol Head Neck Surg* 2004; 131: 864-70). The biomaterial approach has been problematic because durable biomaterials that also have the appropriate viscoelastic properties have yet to be developed. Current biomaterials are all too stiff to be injected into the lamina propria compartment.

The ability to take cells from an individual, expand those cells in the laboratory, and inject them into the same individual to repair symptomatic tissue defects is a newly evolving therapeutic modality in medicine. Initial work in this area of "cultured autologous cellular" therapy was directed towards chondrocytes. A Federal Drug Administration (FDA) approved autologous cultured chondrocyte product (Carticel®, Genzymebiosurgery, Cambridge, Mass.) has been available since 1997 for orthopedic use (Hayflick L and Moorhead P S. *Exp Cell Research* 1961; 25:585-621). Autologous cellular therapy has also been applied clinically to include transplantation of autologous cultured melanocytes for treatment of segmental vitiligo (Treco D A et al. Fibroblast cell biology and gene therapy. In: Chang P L, ed. Somatic Gene Therapy. Boca Raton: CRC Press, 1995:49-60), autologous keratinocytes for treatment of ulcers and burns (Jacobson et al. *Am J Speech Lang Pathol* 1997; 6:66-70; Hartnick et al. *Laryngoscope* 2005; 115:4-15), and autologous fibroblasts for treatment of facial wrinkles (Boss et al. *Ann Plast Surg* 2000; 44:536-42; Watson et al. *Arch Facial Plast Surg* 1999; 1:165-70; Kanemaru et al *Ann Otol Rhinol Laryngol* 2003; 112:915-920). No adverse effects such as malignant transformation of injected cells or significant tissue reaction have been reported so far with the use of autologous cellular therapy.

The lamina propria layer is composed primarily of ECM molecules such as collagen, elastin, and proteoglycans. Fibroblast cells in this layer produce these ECM molecules (Gray, et al., 1999). Theoretically, injection of autologous fibroblasts into the lamina propria layer could lead to reconstitution of normal lamina propria ECM components and improve the voice disorder by re-establishing normal mucosal pliability of the vocal folds. Lamina propria replacement therapy must consider the complex three dimensional organization of this layer that develops and matures over a significant time period. At birth, the lamina propria layer is a hyper-cellular monolayer and it matures over the next seven to thirteen years into the trilaminar layer with the differential fiber and proteoglycan composition seen in adults. This three dimensional organization is complex with not only differences in the relative composition of the ECM molecules within the layer but also in the three dimensional orientation of collagen and elastic fibers. Lamina propria replacement therapy therefore needs to address not only the viscoelasticity of the replacement material but its three-dimensional geometry and composition as well. Production of such lamina propria with its normal components in proper concentration and configuration remains a daunting task with currently available tissue engineering techniques.

Fibroblasts are readily obtained from skin or buccal mucosa by punch biopsy and can be cultured free of other cell types. Human fibroblasts do not spontaneously become immortal in culture, a property that has significant implications when their re-injection into a human being is considered. Cultured autologous fibroblast therapy in humans has so far been directed mainly in the cosmetic plastic surgery field for the treatment of facial wrinkles and scars (Boss et al. *Ann Plast Surg* 2000; 44:536-42; Watson et al. *Arch Facial Plast Surg* 1999; 1:165-70; Kanemaru et al. *Ann Otol Rhinol Laryngol* 2003; 112:915-920). Boss and colleagues reported treating 1,000 subjects with cultured autologous fibroblasts. They performed approximately 4,000 injections from 1995 through 1999. The follow-up period was 36-48 months. Ninety-two percent of the subjects were satisfied with the therapy. There were a total of 13 reported reactions (0.27%) to the injections, of which 11 were mild reactions with redness and swelling that resolved within 48-72 hours. The other two reactions were moderate with swelling and erythema for 7-10 days. Watson and colleagues reported a 6-month prospective pilot study in 10 adults to assess the efficacy of cultured autologous fibroblasts to treat skin wrinkles and dermal depressions. Microscopic examination of the injection site was also performed and demonstrated a denser and thicker layer of collagen in the dermal region, absence of any inflammatory reaction, and viable fibroblasts throughout. No adverse reactions were noted clinically or microscopically.

A canine study has previously shown the potential for autologous fibroblast injection therapy for treatment of vocal fold scars. Canine lamina propria replacement therapy was performed where autologous fibroblasts were harvested from buccal mucosal biopsies and expanded in the laboratory. Fourth or fifth passage fibroblasts were injected into previously scarified vocal folds. The scarred vocal folds had absent or severely limited mucosal waves and poor acoustic parameters. Significant improvements in mucosal waves and acoustic parameters were obtained following autologous fibroblasts injection therapy. Chhetri D K et al. *Otolaryngol Head Neck Surg* 2004; 131: 864-70). Two months later less atrophy was observed in the treated vocal fold compared to the control vocal fold. Histologically the injected cells appeared viable. However, phonation studies were not performed and the mucosal wave grade or the acoustic quality of voice was not provided. In another study, human embryonic stem cells were injected into scarred rabbit vocal folds and histologic assessment performed one month later (Cedervall, et. al. *Laryngoscope* 2007; 117:2075-2081). Persistence of the embryonic stem cells was observed and the injected vocal fold was associated with decreased viscoelasticity (as measured by parallel plate rheometry) as compared to the untreated but scarred side. Another study performed injection of autologous fibroblasts from skin into scarred rabbit vocal folds. In contrast from other reports, this study "primed" the fibroblasts by addition of various factors such as epidermal growth factor, hepatocyte growth factor (HGF), and decorin to the cell culture (Krishna et al. *Otolaryngol Head Neck Surg* 2006; 135:937-945). They reported that HGF treated cells demonstrated increased synthesis of hyaluronic acid, and the HGF and decorin treated cells demonstrated diminished collagen synthesis in vivo.

While demonstration of appropriate changes to the ECM components is important, ultimately the resulting vibratory behavior of the vocal folds is most important. Specifically, the return of vocal fold mucosal pliability as improved mucosal waves upon phonation should be one of the ultimate criteria for success. One previous animal study has performed autologous fibroblast injection into scarred vocal folds in a canine model and demonstrated return of mucosal waves and improved acoustic parameters (Cedervall et al. *Laryngoscope* 2007; 117:2075-2081). In that study, vocal fold scarring was induced unilaterally in the animals and resulted in absent or severely limited mucosal waves and significantly worse acoustic parameters. Autologous fibroblasts were harvested from the canine buccal mucosa and the cell population was expanded in the laboratory. Fourth or fifth passage fibroblasts were then injected into previously scarified vocal folds. Significant improvements in mucosal waves and acoustic parameters were obtained after lamina propria replacement therapy. After therapy, mucosal waves became normal in four animals and near normal in the other four. No statistical difference was found in mucosal wave grade between baseline and post-therapy. All animals tolerated therapy without complications. Histological analysis of the treated vocal folds demonstrated an increased density of fibroblasts, collagen, and reticulin, a decreased density of elastin, and no change in hyaluronic acid.

It is therefore an object of the present invention to provide defined dosage unit formulations of autologous dermal fibroblasts for injection into human patients for the repair and long term augmentation of vocal cord defects.

It is a further object of the present invention to provide dosage unit formulation that contain stem cells, precursor cells or partially differentiated cells that can be used for the repair and long term augmentation of vocal cord defects in humans.

SUMMARY OF THE INVENTION

Dosage units consist of an autologous cell therapy product composed of fibroblasts grown for each individual to be treated for augmentation or regeneration of vocal cords. The suspension of autologous fibroblasts, grown from a biopsy of each individual's own skin using current good manufacturing practices (CGMP) and standard tissue culture procedures, is supplied in vials containing cryopreserved fibroblasts or precursors thereof, having a purity of at least 98% fibroblasts and a viability of at least 85%, for administration. In a preferred embodiment, from one to six mL, for example two mL, is administered three times approximately three to six weeks apart. In one embodiment, the cells are at a concentration of from $1.0-2.0 \times 10^7$ cells/mL. The autologous fibroblasts are thought to increase the synthesis of extracellular matrix components, including collagen. Dosage and timing of administration have been demonstrated to be critical to achieving clinically significant outcomes.

The example describes a clinical study in which five patients were enrolled with vocal fold scars that ranged from isolated lamina propria loss to full thickness scarring that included the epithelium. All subjects received all treatments and followed up to 12 months. Assessment of safety endpoints showed that the only adverse events were temporary otalgia during treatment injection in the two patients with full thickness cover scars. There was no other morbidity or mortality. There were no laboratory abnormalities or other untoward events that were considered related to the study treatment. The primary efficacy endpoint of change from baseline in the mucosal wave grade showed a sustained improvement from week 8 through the Month 12 visit. A trend for sustained improvements through month 12 was also noted for the VHI, VAS, and Voice Quality Questionnaire.

BRIEF DESCRIPTION OF THE DRAWINGS

FIG. 2 is a standardized manufacturing process flow diagram.

DETAILED DESCRIPTION OF THE INVENTION

I. Autologous Fibroblast Formulation

Figure 1:
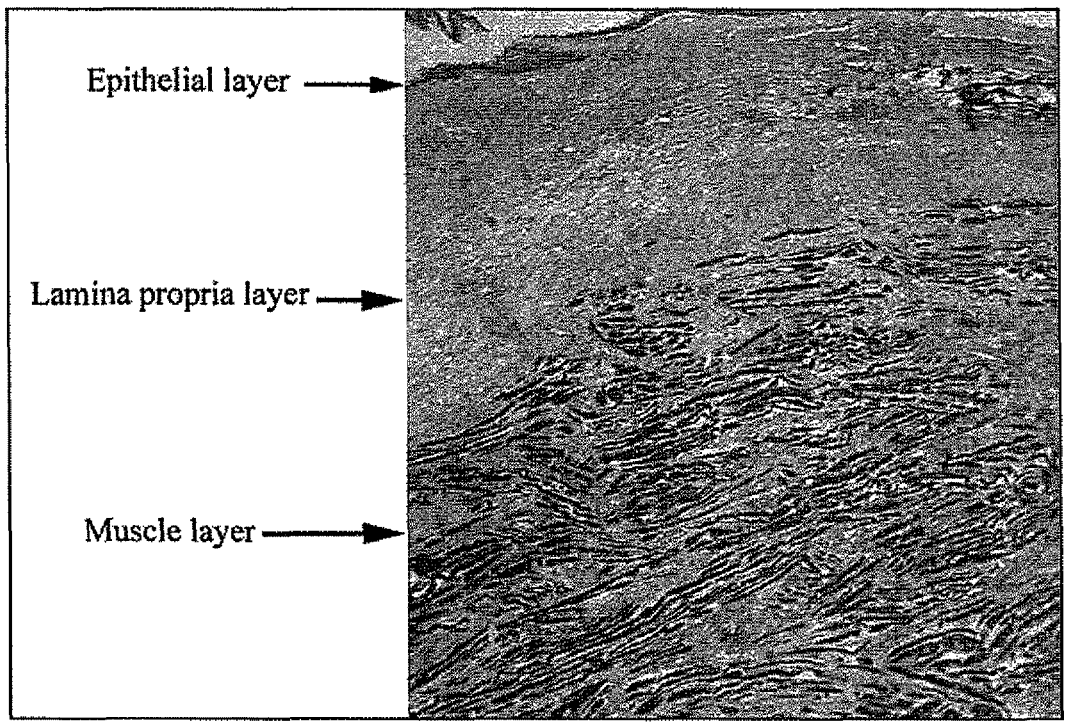
FIG. 1 is a schematic of the anatomy of the vocal folds from Hirano M. *Otologia* (*Fukuoka*) 1975; 21:239-442. The superficial layer is the vocal fold epithelium, followed by the middle lamina propria layer, and the deep muscular layer.

The following definitions are used herein:

ATM Analytical Test Method
AZFICEL-T USAN nomenclature for autologous cultured fibroblasts
BULK HARVEST material following final harvest prior to formulation in cryopreservation media
CGMP Current Good Manufacturing Practice
CS Cell stack
DMEM Dulbecco's Modification of Eagle's Medium
DMSO Dimethyl sulfoxide
DRUG PRODUCT—INJECTION material washed and reformulated in DMEM, vialed and ready for shipment to clinical sites
DRUG SUBSTANCE—CRYOVIAL material formulated in cryopreservation media and aliquoted into cryovials
EDTA Ethylenediaminetetra acetic acid
FACS Fluorescence Activated Cell Sorting
FBS Fetal Bovine Serum
GA Gentamicin and Amphotericin B
IMDM Iscove's Modified Dulbecco's Medium
IND Investigational New Drug application
PBS Phosphate Buffered Saline
PCA Personal Cell Analysis
QC Quality Control
USP United States Pharmacopeia A. Sources of Cells 1. Autologous Dermal Fibroblasts An autologous fibroblast product has been developed. The cell therapy product is composed of a suspension of autologous fibroblasts, grown from a biopsy of each individual's own skin using standard tissue culture procedures. Skin tissue (dermis and epidermis layers) is biopsied from a patient's post-auricular area and shipped via next day delivery to a manufacturing facility at 2-8° C. Fibroblasts isolated from the tissue via enzymatic digestion are expanded to a quantity sufficient for injection into the patient's target treatment area. The Cell therapy product consists of expanded fibroblasts, formulated to the target cell concentration and cryopreserved in cryovials, called Bulk Drug Substance—Cryovial. The final cell therapy product consists of thawed Bulk Cell therapy product—Cryovial cells that are thawed, washed and prepared for patient injection.

The cells in the formulation display typical fibroblast morphologies when growing in cultured monolayers. Specifically, cells may display an elongated, fusiform or spindle appearance with slender extensions, or cells may appear as larger, flattened stellate cells which may have cytoplasmic leading edges. A mixture of these morphologies may also be observed. The cells express proteins characteristic of normal fibroblasts including the fibroblast-specific marker, CD90 (Thy-1), a 35 kDa cell-surface glycoprotein, and the extracellular matrix protein, collagen.

2. Precursor Cells

The fibroblasts can also be used to create other cell types for tissue repair or regeneration. Derivation of embryonic stem (ES) cells genetically identical to a patient by somatic cell nuclear transfer (SCNT) holds the potential to cure or alleviate the symptoms of many degenerative diseases while circumventing concerns regarding rejection by the host immune system. Byrne, et al., *Nature* 2007 22; 450(7169): 497-502, used a modified SCNT approach to produce rhesus macaque blastocysts from adult skin fibroblasts, and successfully isolated two ES cell lines from these embryos. DNA analysis confirmed that nuclear DNA was identical to donor somatic cells and that mitochondrial DNA originated from oocytes. Both cell lines exhibited normal ES cell morphology, expressed key stem-cell markers, were transcriptionally similar to control ES cells and differentiated into multiple cell types in vitro and in vivo. See also Sparman, et al. *Stem Cells.* 2009; 27(6):1255-64, Hochedlinger, et al., *Development.* 2009 February; 136(4):509-23 and Kanawaty, et al. *Bioessays.* 2009 February; 31(2):134-8.

Methods are known by which fibroblasts can be de-differentiated into pluripotent cells: cell fusion (Cowan et al. Science. 2005 Aug. 26; 309(5739):1369-73), direct reprogramming (Takahashi, et al., *Cell.* 2007 30; 131(5):861-72), and somatic cell nuclear transfer (Byrne, et al. 2007). Takahashi, et al. demonstrated the generation of iPS cells from adult human dermal fibroblasts with the same four factors: Oct3/4, Sox2, Klf4, and c-Myc. Human iPS cells were similar to human embryonic stem (ES) cells in morphology, proliferation, surface antigens, gene expression, epigenetic status of pluripotent cell-specific genes, and telomerase activity. Furthermore, these cells could differentiate into cell types of the three germ layers in vitro and in teratomas. These findings demonstrate that iPS cells can be generated from adult human fibroblasts.

B. Preparation of Cells

The autologous fibroblasts in the Drug Substance are derived by enzymatic digest of a biopsy of the recipient's own skin followed by expansion in culture using standard cell culture techniques Skin tissue (dermis and epidermis layers) is biopsied from a subject's post-auricular area. The starting material is composed of three mm punch buccal mucosa biopsies collected using standard aseptic practices. Buccal mucosa rather than skin biopsy is used as the source for autologous fibroblasts for treatment of vocal cord scarring because the collagen production profile of buccal mucosa more closely parallels that of the vocal fold fibroblasts as compared to dermal fibroblasts. (Hayflick L and Moorhead P S. Exp Cell Research 1961; 25:585-621; Treco D A et al. In: Chang P L, ed. Somatic Gene Therapy. Boca Raton: CRC Press, 1995:49-60). Although buccal mucosa is the preferred test location, biopsies may be sourced from another location in the mouth, such as hard palette. The biopsies are collected by the treating physician, placed into a vial containing sterile phosphate buffered saline (PBS). The biopsies are shipped in a 2-8° C. refrigerated shipper back to the manufacturing facility. After arrival at the manufacturing facility, the biopsy is inspected and, upon acceptance, transferred directly to the manufacturing area.

Upon initiation of the process, the biopsy tissue is then washed prior to enzymatic digestion. After washing, a Liberase Digestive Enzyme Solution is added without mincing, and the biopsy tissue is incubated at 37.0 ±2° C. for one hour. Time of biopsy tissue digestion is a critical process parameter that can affect the viability and growth rate of cells in culture. Liberase is a collagenase/neutral protease enzyme cocktail obtained formulated from Lonza Walkersville, Inc. (Walkersville, Md.) and unformulated from Roche Diagnostics Corp. (Indianapolis, Ind.). Alternatively, other commercially available collagenases may be used, such as Serva Collagenase NB6 (Helidelburg, Germany). After digestion, Initiation Growth Media (IMDM, GA, 10% Fetal Bovine Serum (FBS)) is added to neutralize the enzyme, cells are pelleted by centrifugation and resuspended in Initiation Growth Media. Alternatively, centrifugation is not performed, with full inactivation of the enzyme occurring by the addition of Initiation Growth Media only. Initiation Growth Media is added prior to seeding of the cell suspension into a T-175 cell culture flask for initiation of cell growth and expansion. A T-75, T-150, T-185 or T-225 flask can be used in place of the T-75 flask. Cells are incubated at 37±2.0° C. with 5.0±1.0% $CO_2$ and fed with fresh Complete Growth Media every three to five days. All feeds in the process are performed by removing half of the Complete Growth Media and replacing the same volume with fresh media. Alternatively, full feeds can be performed. Cells should not remain in the T-175 flask greater than 30 days prior to passaging. Confluence is monitored throughout the process to ensure adequate seeding densities during culture splitting.

When cell confluence is greater than or equal to 40% in the T-175 flask, they are trypsinized and seeded into a T-500 flask for continued cell expansion. Alternately, one or two T-300 flasks, One Layer Cell Stack (1 CS), One Layer Cell Factory (1 CF) or a Two Layer Cell Stack (2 CS) can be used in place of the T-500 Flask. Morphology is evaluated at each passage and prior to harvest to monitor the culture purity throughout the process. Morphology is evaluated by comparing the observed sample with visual standards for morphology examination of cell cultures. The cells display typical fibroblast morphologies when growing in cultured monolayers. Cells may display either an elongated, fusiform or spindle appearance with slender extensions, or appear as larger, flattened stellate cells which may have cytoplasmic leading edges. A mixture of these morphologies may also be observed. Fibroblasts in less confluent areas can be similarly shaped, but randomly oriented. The presence of keratinocytes in cell cultures is also evaluated. Keratinocytes appear round and irregularly shaped and, at higher confluence, they appear organized in a cobblestone formation. At lower confluence, keratinocytes are observable in small colonies.

Cells are incubated at 37±2.0° C. with 5.0±1.0% $CO_2$ and fed every three to five days in the T-500 flask and every five to seven days in the ten layer cell stack (10 CS). Cells should not remain in the T-500 flask for more than 10 days prior to passaging. QC release testing for safety of the Bulk Drug Substance includes sterility and endotoxin testing. When cell confluence in the T-500 flask is ≥95%, cells are passaged to a 10 CS culture vessel. Alternately, two Five Layer Cell Stacks (5 CS) or a 10 Layer Cell Factory (10 CF) can be used in place of the 10 CS. Passage to the 10 CS is performed by removing the spent media, washing the cells, and treating with Trypsin-EDTA to release adherent cells in the flasks into the solution. Additional Complete Growth Media is added to neutralize the trypsin and the cells from the T-500 flask are pipetted into a 2 L bottle containing fresh Complete Growth Media. The contents of the 2 L bottle are transferred into the 10 CS and seeded across all layers. Cells are then incubated at 37±2.0° C. with 5.0±1.0% $CO_2$ and fed with fresh Complete Growth Media every five to seven days. Cells should not remain in the 10 CS for more than 20 days prior to passaging.

Primary Harvest: When cell confluence in the 10 CS is 95% or more, cells are harvested. Harvesting is performed by removing the spent media, washing the cells, treating with Trypsin-EDTA to release adherent cells into the solution, and adding additional Complete Growth Media to neutralize the trypsin. Cells are collected by centrifugation, resuspended, and in-process Quality Control (QC) testing performed to determine total viable cell count and cell viability.

If additional cells are required after receiving cell count results from the primary 10 CS harvest, an additional passage into multiple cell stacks (up to four 10 CS) is performed (Step 5a in FIG. 1). For additional passaging, cells from the primary harvest are added to a 2 L media bottle containing fresh Complete Growth Media. Resuspended cells are added to multiple cell stacks and incubated at 37±2.0° C. with 5.0±1.0% $CO_2$. The cell stacks are fed and harvested as described above, except cell confluence must be 80% or higher prior to cell harvest. The harvest procedure is the same as described for the primary harvest above. A mycoplasma sample from cells and spent media is collected, and cell count and viability performed as described for the primary harvest above.

Alternate Manufacturing Methods

Alternatively, cells can be passaged from either the T-175 flask (or alternatives) or the T-500 flask (or alternatives) into a spinner flask containing microcarriers as the cell growth surface. Microcarriers are small bead-like structures that are used as a growth surface for anchorage dependent cells in suspension culture. They are designed to produce large cell yields in small volumes.

In this apparatus, a volume of Complete Growth Media ranging from 50 mL-300 mL is added to a 500 mL, IL or 2 L sterile disposable spinner flask. Sterile microcarriers are added to the spinner flask. The culture is allowed to remain static or is placed on a stir plate at a low RPM (15-30 RRM) for a short period of time (1-24 hours) in a 37±2.0° C. with 5.0±1.0% $CO_2$ incubator to allow for adherence of cells to the carriers. After the attachment period, the speed of the spin plate is increased (30-120 RPM). Cells are fed with fresh Complete Growth Media every one to five days, or when media appears spent by color change.

Cells are collected at regular intervals by sampling the microcarriers, isolating the cells and performing cell count and viability analysis. The concentration of cells per carrier is used to determine when to scale-up the culture. When enough cells are produced, cells are washed with PBS and harvested from the microcarriers using trypsin-EDTA and seeded back into the spinner flask in a larger amount of microcarriers and higher volume of Complete Growth Media (300 mL-2 L). Alternatively, additional microcarriers and Complete Growth Media can be added directly to the spinner flask containing the existing microcarrier culture, allowing for direct bead-to-bead transfer of cells without the use of trypsiziation and reseeding. Alternatively, if enough cells are produced from the initial T-175 or T-500 flask, the cells can be directly seeded into the scale-up amount of microcarriers. After the attachment period, the speed of the spin plate is increased (30-120 RPM). Cells are fed with fresh Complete Growth Media every one to five days, or when media appears spent by color change. When the concentration reaches the desired cell count for the intended indication, the cells are washed with PBS and harvested using trypsin-EDTA.

Microcarriers used within the disposable spinner flask may be made from poly blend such as BioNOC II® (Cesco Bioengineering, distributed by Bellco Biotechnology, Vineland, N.J.) and FibraCel® (New Brunswick Scientific, Edison, N.J.), gelatin, such as Cultispher-G (Percell Biolytica, Astrop, Sweden), cellulose, such as Cytopore™ (GE Healthcare, Piscataway, N.J.) or coated/uncoated polystyrene, such as 2D MicroHex™ (Nunc, Weisbaden, Germany), Cytodex® (GE Healthcare, Piscataway, N.J.) or Hy-Q Sphere™ (Thermo Scientific Hyclone, Logan, Utah).

Alternatively, cells can be processed on poly blend 2D microcarriers such as BioNOC II® and FibraCel® using an automatic bellow system, such as FibraStage™ (New Brunswick Scientific, Edison, N.J.) or BelloCell® (Cesco Bioengineering, distributed by Bellco Biotechnology, Vineland, N.J.) in place of the spinner flask apparatus. Cells from the T-175 (or alternatives) or T-500 flask (or alternatives) are passaged into a bellow bottle containing microcarriers with the appropriate amount of Complete Growth Media, and placed into the system. The system pumps media over the microcarriers to feed cells, and draws away media to allow for oxygenation in a repeating fixed cycle. Cells are monitored, fed, washed and harvested in the same sequence as described above.

Alternatively, cells can be processed using automated systems. After digestion of the biopsy tissue or after the first passage is complete (T-175 flask or alternative), cells may be seeded into an automated device. One method is an Automated Cellular Expansion (ACE) system, which is a series of commercially available or custom fabricated components linked together to form a cell growth platform in which cells can be expanded without human intervention. Cells are expanded in a cell tower, consisting of a stack of disks capable of supporting anchorage-dependent cell attachment. The system automatically circulates media and performs trypsiziation for harvest upon completion of the cell expansion stage.

Alternatively, the ACE system can be a scaled down, single lot unit version comprised of a disposable component that consists of cell growth surface, delivery tubing, media and reagents, and a permanent base that houses mechanics and computer processing capabilities for heating/cooling, media transfer and execution of the automated programming cycle.

Upon receipt, each sterile irradiated ACE disposable unit will be unwrapped from its packaging and loaded with media and reagents by hanging pre-filled bags and connecting the bags to the existing tubing via aseptic connectors. The process continues as follows:

Inside a biological safety cabinet (BSC), a suspension of cells from a biopsy that has been enzymatically digested is introduced into the "pre-growth chamber" (small unit on top of the cell tower), which is already filled with Initiation Growth Media containing antibiotics. From the BSC, the disposable would be transferred to the permanent ACE unit already in place.

After approximately three days, the cells within the pre-growth chamber are trypsinized and introduced into the cell tower itself, which is pre-filled with Complete Growth Media. Here, the "bubbling action" caused by $CO_2$ injection force the media to circulate at such a rate that the cells spiral downward and settle on the surface of the discs in an evenly distributed manner.

For approximately seven days, the cells are allowed to multiply. At this time, confluence will be checked (method unknown at time of writing) to verify that culture is growing. Also at this time, the CGM will be replaced with fresh CGM. CGM is replaced every seven days for three to four weeks. At the end of the culture period, the confluence is checked once more to verify that there is sufficient growth to possibly yield the desired quantity of cells for the intended treatment.

If the culture is sufficiently confluent, it is harvested. The spent media (supernatant) is drained from the vessel; PBS is pumped into the vessel (to wash the media, FBS from the cells) and drained almost immediately; trypsin-EDTA is pumped into the vessel to detach the cells from the growth surface; the trypsin/cell mixture is drained from the vessel and enter the spin separator; cryopreservative is pumped into the vessel to rinse any residual cells from the surface of the discs, and be sent to the spin separator as well; the spin separator collects the cells and then evenly resuspend the cells in the shipping/injection medium; from the spin separator, the cells will be sent through an inline automated cell counting device or a sample collected for cell count and viability testing via laboratory analyses. Once a specific number of cells has been counted and the proper cell concentration has been reached, the harvested cells are delivered to a collection vial that can be removed to aliquot the samples for cryogenic freezing.

Alternatively, automated robotic systems may be used to perform cell feeding, passaging, and harvesting for the entire length or a portion of the process. Cells can be introduced into the robotic device directly after digest and seed into the T-175 flask (or alternative). The device may have the capacity to incubate cells, perform cell count and viability analysis and perform feeds and transfers to larger culture vessels. The system may also have a computerized cataloging function to track individual lots. Existing technologies or customized systems may be used for the robotic option, such as the products obtained from The Automation Partnership (TAP).

C. Preparation of Cell Suspension

At the completion of culture expansion, the cells are harvested and washed, then formulated to contain $1.0$-$2.7 \times 10^7$ cells/mL, with a target of $2.2 \times 10^7$ cells/mL. Alternatively, the target can be adjusted within the formulation range to accommodate different indication doses. The drug substance consists of a population of viable, autologous human fibroblast cells suspended in a cryopreservation medium consisting of Iscove's Modified Dulbecco's Medium (IMDM) and Profreeze-CDM™ (Lonza, Walkerville, Md.) plus 7.5% dimethyl sulfoxide (DMSO). Alternatively, a lower DMSO concentration may be used in place of 7.5%. Alternatively, CryoStor™ CS5 or CryoStor™ CS10 (BioLife Solutions, Bothell, Wash.) may be used in place of IMDM/Profreeze/DMSO.

After completion of the controlled rate freezing step, Bulk Drug Substance vials are transferred to a cryogenic freezer for storage in the vapor phase. After cryogenic freezing, the Drug Substance is submitted for Quality Control testing. Drug Substance specifications also include cell count and cell viability testing performed prior to cryopreservation and performed again for Drug Substance—Cryovial. Viability of the cells must be 85% or higher for product release. Cell count and viability are conducted using an automated cell counting system (Guava Technologies), which utilizes a combination of permeable and impermeable fluorescent, DNA-intercalating dyes for the detection and differentiation of live and dead cells. Alternatively, a manual cell counting assay employing the trypan blue exclusion method may be used in place of the automated cell method above or other automated cell counting systems may be used to perform the cell count and viability method, including Cedex (Roche Innovatis AG, Bielefield, Germany), ViaCell™ (Beckman Coulter, Brea, Calif.), NuceloCounter™ (New Brunswick Scientific, Edison, N.J.), Countless® (Invitrogen, division of Life Technologies, Carlsbad, Calif.), or Cellometer® (Nexcelom Biosciences, Lawrence, Mass.). Drug Substance—Cryovial samples must meet a cell count specification of $1.0$-$2.7 \times 10^7$ cells/mL prior to release. Sterility and endotoxin testing are also conducted during release testing.

In addition to cell count and viability, purity/identity of the Drug Substance is performed and must confirm the suspension contains 98% or more fibroblasts. The usual cell contaminants include keratinocytes. The purity/identify assay employs fluorescent-tagged antibodies against CD90 and CD104 (cell surface markers for fibroblast and keratinocyte cells, respectively) to quantify the percent purity of a fibroblast cell population. CD90 (Thy-1) is a 35 kDa cell-surface glycoprotein. Antibodies against CD90 protein have been shown to exhibit high specificity to human fibroblast cells. CD104, integrin β4 chain, is a 205 kDa transmembrane glycoprotein which associates with integrin α6 chain (CD49f) to form the α6/β4 complex. This complex has been shown to act as a molecular marker for keratinocyte cells (Adams and Watt 1991). Antibodies to CD104 protein bind to 100% of human keratinocyte cells. Cell count and viability is determined by incubating the samples with Viacount Dye Reagent and analyzing samples using the Guava PCA system. The reagent is composed of two dyes, a membrane-permeable dye which stains all nucleated cells, and a membrane-impermeable dye which stains only damaged or dying cells. The use of this dye combination enables the Guava PCA system to estimate the total number of cells present in the sample, and to determine which cells are viable, apoptotic, or dead.

D. Dosage Units

Drug Substance—Cryovial used to prepare the final dosage unit consists of fibroblasts that are harvested from the final culture vessel, formulated to the desired cell concentration and cryopreserved in cryovials. Drug Substance—Cryovial is stored in a cryopreservation medium consisting of IMDM and Profreeze™ plus 7.5% DMSO to a target of $2.2 \times 10^7$ cells/mL. After exposure to a controlled rate freezing cycle, the cryovialed Drug Substance is stored frozen in the vapor phase of a liquid nitrogen freezer.

Harvested cells are pooled, formulated in a cryopreservation media that includes Profreeze, DMSO and IMDM media, aliquoted into cryovials and stored frozen in liquid nitrogen as the Drug Substance—Cryovial material via controlled rate freezing.

The caps and vials are radiation sterilized and received sterile from the manufacturer. The required volume of bulk material needed for treatment is removed from frozen storage, thawed, and pooled. The cells are washed with 4× bulk volume of PBS and centrifuged at 150×g for 10 minutes (5±3° C.). This is followed by a wash with 4× bulk volume of DMEM by resuspension and centrifugation at 150×g for 10 minutes (5±3° C.). The washed cells are resuspended in DMEM without phenol red to a target concentration of $1.0$-$2.0 \times 10^7$ cells/mL. Alternatively, the second 4× wash and final resuspension can be performed with Hypothermosol®-FRS (BioLife Solutions, Bothell, Wash.). The final sterile cryovial containers are then manually filled in a Biological Safety Cabinet to a volume of 1.2 mL/container. The Drug Product—Injection is stored at 2-8° C. until shipment in a 2-8° C. refrigerated shipper to the administration site. Alternatively, Drug Substance vials can be removed from cryogenic storage and shipped directly to the administration site for dilution and administration. In the direct injection concept, the cells are harvested and prepared for cryopreservation at a higher cell concentration ($3.0$-$4.0 \times 10^7$ cell/mL as compared to the current target of $2.2 \times 10^7$ cells/mL). When an injection is pending, the frozen vial will be shipped to the study site on dry ice or in a liquid nitrogen dewar. The administration site thaws the vial by hand or with a heat block, and performs a 1:1 ratio dilution of the frozen cells at the study site using a typical injection diluent such as bacteriostatic water, sterile water, sodium chloride, or phosphate buffered saline. Alternatively, DMEM may be used as the diluent. This concept eliminates the need to wash and prepare a fresh suspension of the injection for overnight shipment to the study site.

Alternatively, cells freshly harvested from flasks or cells stacks can be adjusted to a target concentration of $1.0$-$2.0 \times 10^7$ cells/mL in DMEM, undergo all Bulk Harvest and Drug Substance—Cryovial testing described above and shipped fresh overnight to the administration site in a 2-8° C. refrigerated shipper as the final injection product. In this scenario, sterility and mycoplasma testing may be performed upstream from the harvest to allow time for results prior to shipment.

II. Methods of Administration

A. Preparation of Dosage Units

A suspension of each patient's own living autologous fibroblasts formulated in Dulbecco's Modified Eagle's Medium (DMEM) without phenol red is supplied as two 2 mL vials with each vial containing 1.2 mL of fibroblasts at $1.0$-$2.0 \times 10^7$ cells/mL. A dose range from $1.1$-$5.8 \times 10^7$ cells/mL injection has been used successfully.

B. Administration of Dosage Units

Vials are warmed to room temperature and gently inverted to resuspend the settled cells. The cellular suspension is withdrawn from the container using a small unit syringe fitted with a detachable needle or with a fixed needle. A 27 gauge, 1½ inch needle is required for injection of the product into the vocal folds. However, a syringe with a larger bore (18 or 21-gauge) detachable needle may be used to aid in withdrawing the product from the container. Once withdrawn, the larger-gauge needle can be switched out with a 27-gauge needle and the product administered. Product administration is accomplished using a distal chip flexible fiberoptic laryngoscope to visualize the vocal folds, then advancing the injection needle into the larynx using the trans-cricothyroid membrane technique. The product is then layered in the vocal fold subepithelial layer (in the lamina propria compartment).

C. Conditions to be Treated

Autologous fibroblasts are injected into the lamina propria layer to treat vocal fold scarring. In the preferred treatment regime, three treatment doses of $1$-$2 \times 10^7$ cells/mL are injected into the superficial lamina propria layer of each scarred vocal fold one to eight, preferably four weeks apart.

EXAMPLE 1

A Phase I Clinical Trial to Determine the Safety and Efficacy of Autologous Fibroblast Cellular Injection Therapy for Treatment of Vocal Fold Scarring Objectives: The extracellular matrix and cellular components of the lamina propria layer is lost or altered in vocal fold scars. The goal of this study was to assess the safety and effectiveness of autologous fibroblasts injection to the lamina propria layer to treat vocal fold scarring.

Results: Five patients were enrolled into the study with vocal fold scars that ranged from isolated lamina propria loss to full thickness scarring that included the epithelium. All subjects received all treatments and were followed up to 12 months. Assessment of safety endpoints showed that the only adverse events were temporary otalgia during treatment injection in the two patients with full thickness cover scars. There was no other morbidity or mortality. There were no laboratory abnormalities or other untoward events that were considered related to the study treatment. The primary efficacy endpoint of change from baseline in the mucosal wave grade showed a sustained improvement from week 8 through the Month 12 visit. A trend for sustained improvements through month 12 was also noted for the VHI, VAS, and Voice Quality Questionnaire. No trends for improvement were noted for Harmonic-to-Noise ratio and maximal phonation time.

Conclusions: This study showed that injection of autologous fibroblasts into the scarred vocal fold lamina propria layer is safe. Sustained trends for improved outcome were supported by 12-month data for Mucosal Wave Grade, VHI, VAS Assessment of Vocal Fold Improvement, and Voice Quality Questionnaire.

Methods

I. Overview of Experimental Design

Five subjects with vocal fold scarring who met the inclusion and exclusion criteria were selected from a voice clinic for enrollment. After enrollment into the study, punch biopsies of buccal mucosa were obtained. The biopsy samples are sent to a commercial laboratory for laboratory expansion of the fibroblast cell population. After adequate expansion of the cells, subjects received percutaneous injections of the expanded autologous fibroblasts into the subepithelial layer (lamina propria compartment) of the scarred vocal folds. Subjects received treatment to one or both vocal folds, depending upon whether unilateral or bilateral scarring was present. Only one vocal fold was treated at each treatment session, alternating to the opposite vocal fold (if being treated bilaterally) at the next treatment session. Each scarred vocal fold was treated a total of three times (total of three treatment sessions for unilateral vocal fold scarring and six treatment sessions for bilateral vocal fold scarring).

Safety and efficacy assessments were performed at various time intervals as detailed below. Follow-up examinations were performed at 3, 4, 8, and 12 months following the first injection. Efficacy assessments included laryngeal videostroboscopy, voice recording for acoustic analysis of Harmonic-to-Noise ratio, and completion of questionnaires including the Voice Handicap Index (VHI), visual analog scale (VAS) instrument, and a voice questionnaire.

II. Subjects

Five adults 18 years of age or older were selected for the study. The number of subjects for the study and the plan to inject only one vocal fold per treatment session was decided after careful discussion of the research protocol and the safety of the procedure with representatives of the Federal Drug Administration, who approved the research protocol and the Investigational New Drug Application for this study.

(a) Inclusion Criteria:
(1) At least 18 years of age.
(2) Presence of unilateral or bilateral vocal fold scarring as diagnosed by medical history and videostroboscopic examination of the larynx.
(3) Grade 1-2 mucosal waves (see below for grading) as determined by videostroboscopy.
(4) Failed any one or more alternative treatments including but not limited to anti-reflux regimen, speech therapy, or vocal fold injection laryngoplasty at least 4 months prior to screening.
(5) Self-reported that their voice quality was a major handicap.
(6) If female and capable of bearing children agreed to use a medically acceptable means of birth control during the study and tested negative on a pregnancy test prior to the administration of first treatment.
(7) Willing and able to follow study procedures and instructions.

(b) Exclusion Criteria—Subjects were Excluded from the Study for Presence of any of the Following:
(1) An active smoker.
(2) Had an upper respiratory infection at baseline (subject could be rescheduled).
(3) Was already participating, or had within 30 days prior to enrollment participated in another clinical trial involving therapeutic intervention.
(4) Had other concurrent laryngeal pathology including lesions that would require removal.

III. Study Procedures—Subjects Underwent the Following Study Related Procedures:

(a) Buccal Mucosal Biopsy

After enrollment into the study, 3-mm punch biopsies were taken from the buccal mucosa of the subject under clean conditions. Three biopsies were taken and the tissue was sent via overnight courier to a commercial cell production facility (Isolagen Technologies, Inc., Exton, Pa.) for growth and expansion of fibroblast cells. The biopsy was placed in a vial with media that maintained viability of the specimen for at least 48 hours and then shipped immediately in controlled ambient temperature packaging. Buccal mucosa rather than skin biopsy was chosen as the source for autologous fibroblasts because the collagen production profile of mucosa parallels that of the vocal fold fibroblasts as compared to dermal fibroblasts (Krishna et al. *Otolaryngol Head Neck Surg* 2006; 135:937-945). In addition, buccal mucosa is easier to biopsy, leaves no visible external scar, and heals very well without suture closure of the biopsy defect.

(b) Laboratory Expansion of Autologous Fibroblasts

Once received by the laboratory, the buccal mucosal biopsy was digested using a Liberase and seeded into a culture flask with Iscove's Modified Dulbecco's Medium (IM DM) and GA, which was used throughout the cell culture protocol. When a fibroblast cellular monolayer was established it was digested with trypsin to liberate fibroblasts. The fibroblasts were then cultured in larger flasks. When cells reached the established confluence specification, they were treated with trypsin and transferred to a larger flask with IMDM. When adequate cellular expansion had occurred (between 4th to 6th passages), screening and in-process controls for bacterial, fungal and mycoplasma contamination, cell morphology, and confluence of monolayers were completed, and the expanded autologous fibroblasts were harvested into IMDM. The harvested cells suspension was mixed with a cryopreservant containing a low concentration of dimethylsulfoxide (DMSO) for cryopreservation. The cryopreserved cells could be recultured or simply washed and prepped to remove DMSO and replace the remaining medium with DMEM prior to shipping for injection. Cell counts, viability, endotoxin testing, Gram stain, and a final sterility test were then performed on each cell suspension. To complete the injection preparation process, 1.2 mL ($1.0$-$2.0 \times 10^7$ cells) of the final product was filled in a 2 mL cryovial, packaged in an insulated vial container and shipped at 2-8° C. to the treating facility for vocal fold injection. Upon receipt the vial was stored in a refrigerator at 4° C. until ready for injection.

(c) Preparation of Cells for Injection

All vials were received by the study site on the morning of injection and were prepared in the same manner. Shortly before the administration of autologous fibroblasts, the subject's treatment vial was taken out of the refrigerator and allowed to warm to room temperature. The cells were re-suspended by gently inverting the injection vial three times before aseptically drawing the vial's contents into a sterile syringe with an 18-gauge needle. Before administration of autologous cells, the 18-gauge needle was replaced with a 27-gauge, 1½-inch needle.

(d) Vocal Fold Injection

All injections were performed by the investigator who routinely performs in-office injection laryngoplasty. Subject was seated comfortably on an examination chair with the neck slightly extended to expose laryngeal landmarks. The nasal cavity was decongested with neosynephrine, and the nasal cavity and larynx are anesthetized with topical 4% lidocaine spray. The neck skin was not routinely anesthetized unless requested by the subject or it was felt that injection would go smoother if the neck skin was anesthetized. A distal chip flexible fiberoptic laryngoscope (VNL 1170K, KayPentax, Lincoln Park, N.J.) connected to a video monitor was passed via the nostril into the nasal cavity and advanced to the hypopharynx until the vocal folds were visualized. The needle entry site on the anterior neck skin was prepped with alcohol swab. The injection needle was advanced into the larynx using the trans-cricothyroid membrane technique. While visualizing on the video monitor, autologous cells were layered in the vocal fold subepithelial layer (in the lamina propria compartment). Appropriate placement was confirmed visually as expansion of the epithelial layer due to superficial injection. Subjects were observed in the clinic for one hour prior to discharge. Prophylactic antibiotics were not prescribed.

(e) Other Therapy

No other vocal fold therapies were permitted in conjunction with the study treatments and for the duration of follow-up through 12 months.

IV. Assessment of Safety.

Assessments of subject safety included strict maintenance of case report forms (CRFs), tabulations of the incidence of adverse events (AEs), and analysis of changes from baseline in laboratory values.

V. Assessment of Efficacy (a) Summary of Efficacy Endpoints

The primary efficacy endpoint was the absolute change from baseline in mucosal wave grade using videostroboscopy (described below) on each treated vocal fold. Efficacy endpoints were collected at week 4, week 8, month 3, month 4, month 8, and month 12 after first injection treatment.

The secondary efficacy endpoints of this feasibility study were the following outcomes measures (described below):

(1) Subject's impression of improvement in voice quality using a Visual Analog Scale (VAS)
(2) Subject's impression of improvement in voice quality using questionnaire
(3) Absolute change from baseline in the Harmonic-to-Noise ratio (dB) as measured from acoustic analysis of voice
(4) Absolute change from baseline in the Voice Handicap Index (VHI)
(5) Absolute change from baseline in maximum phonation time (MPT)

(b) Clinical Assessments (1) Videostroboscopy:

The primary effect assessment was the absolute change from baseline in mucosal wave grade using videostroboscopy. The investigator performed all videostroboscopic procedures. Both a 70 degree rigid endoscope and a distal chip flexible fiberoptic endoscope were used initially for videostroboscopy. It was determined that the mucosal wave grade in each patient was the same for both endoscopes and therefore the rigid endoscope was used for most of the study period due to its superior optical quality. During the videostroboscopic procedure the endoscope attached to a miniature video camera was used to visualize the larynx under stroboscopic light source. The subject was asked to phonate a sustained vowel "e" and the vocal fold vibration was recorded digitally on a computer for analysis. The recordings were reviewed later by a laryngologist and an experienced speech pathologist and a consensus was generated on the mucosal wave grade. Mucosal waves were graded as follows: 1=absent; 2=limited to the most medial edge of the vocal folds; 3=present laterally up to ¼ of the width of the vocal folds; 4=present up to but less than ½ the width of the vocal folds; 5=present at more than ½ the width of the vocal folds (normal).

(2) Voice Recording for Acoustic Analysis

A sample of voice (a continuous vowel sound /a/) was recorded and digitized to measure acoustic parameters of voice using computer software. Acoustic parameters include Harmonic-to-Noise ratio, jitter, and shimmer. Only Harmonic-to-Noise ratio was calculated because the acoustic measures of jitter and shimmer have not been found to be robust in perception of voice quality. In a pathologic voice, Harmonic-to-Noise ratio is decreased. Another acoustic parameter measured was maximal phonation time (MPT). MPT was defined as the length of time in seconds a subject was able to phonate a sustained vowel in one single deep breath and was averaged over three attempts. Glottic incompetence is typically present in vocal fold scars and sometimes leads to excessive airflow loss from decreased glottic resistance if the glottic gap is large.

(3) Voice Handicap Index (VHI)

Subjects completed a Voice Handicap Index (VHI) survey, which is a 30-item test, developed by Jacobson and colleagues with 10 items in three subscales: emotional, physical, and functional. Each item is answered on a 5-point scale from "0", indicating the subject never felt this about the voice problem to "4", where the subject always felt this to be the case. Thus highest VHI rating per subscale is 40 points and for the entire survey 120 points. Each subscale has been found to be significantly different if it changes by eight points, whereas the total VHI score was found to be significantly different if it changes by 18 points.

(4) Subject's VAS Assessment of Vocal Fold Improvement

Subjects were asked to rate the vocal fold improvement using a Visual Analog Scale (VAS). The VAS will range from "Worst Possible Change From Baseline" on the left side to "Most Possible Improvement From Baseline" on the right side. The VAS at each assessment were measured and given a score from −50 to 50.

(5) Subject's Impression of Voice Quality Questionnaire

Subjects were asked two questions to assess the subject's satisfaction with treatment with the following answer choices:

1. How has your voice quality changed since baseline?
   a. Improved b. No Change c. Worsened
2. Do you consider the treatment a success?
   a. Yes b. No At each assessment, the proportion of subjects that reported each response was tabulated, and 95% confidence intervals calculated.

VI. Statistical Considerations

Version 8.0 or higher of the SAS® statistical software package was used to perform all statistical analyses. When there were missing values statistical evaluations were performed using non-missing values.

Sample size: There was insufficient clinical experience on how this new procedure would affect vocal fold scarring to estimate sample size. The decision to limit sample size to five was selected after discussion with the FDA. The sample size is, however, typical of an exploratory, early phase study in which the objective is to investigate the feasibility of treatment administration Safety Endpoints: Assessments of subject safety included tabulations of the incidence of adverse events and analysis of the percentage change from baseline in laboratory measurements. Laboratory measurements were investigated by calculating the percentage changes from baseline and determining if a statistically significant change from baseline was detected using a paired t-test. Each laboratory result was also flagged as low (L), high (H) and normal (N) based on the lab normal range. Adverse events with an onset during the course of study were recorded and tabulated.

Efficacy Endpoints: The primary effect endpoint analysis of change from baseline in mucosal wave grade using videostroboscopy on each treated vocal fold was assessed with Wilcoxon Signed-Rank test. Secondary effects analysis of changes in Maximal Phonation Time and Harmonic-to-Noise ratio was tested using the Wilcoxon Signed-Rank test. The VAS at each assessment was measured and given a score from −50 to 50. Summary statistics on this change from baseline was provided and tested for differences from zero using the Wilcoxon Signed-Rank test. The Subject's Impression of Voice Quality Questionnaire was evaluated by tabulating the proportion of subjects that report each response, and 95% confidence intervals calculated. The VHI findings were reported individually for each subscale and for the entire survey. Each subscale has been found to be significantly different if it changes by eight points, whereas the total VHI score has been found to be significantly different if it changes by 18 points.

Results

Subjects:

Five subjects who were evaluated in a voice clinic for dysphonia and met inclusion and exclusion criteria were enrolled and completed the study. Three (60%) were male and two (40%) were female. The average age was 55 years, with a range of 35 to 68 years and a median age of 58 years. All five were Caucasian. Prior treatments included anti-reflux medication (5 of 5, 100%), speech therapy (5 of 5, 100%), injection augmentation laryngoplasty with collagen (3 of 5, 60%), and other (2 of 5, 40%). All were in good health and none had a history of tobacco use. Four patients were taking concomitant medications (analgesics, antacids, anti-inflammatory medications, etc.) but none of these were expected to affect the analysis of safety or efficacy of treatment. All five subjects received all scheduled treatments with autologous fibroblasts. The subjects represented the spectrum of vocal fold scars from isolated lamina propria loss to full thickness cover defect as follows:

Subject 1 was a 35 years old male who noted onset of dysphonia after a tonsillectomy five years prior to enrollment in this study. Other associated medical disorders included possible gastroesophageal reflux disease (GERD). Prior therapies for dysphonia included anti-reflux regimen and voice therapy. Videostroboscopic exam at enrollment revealed grade 2 mucosal waves bilaterally and incomplete glottic closure. There were no defects on the epithelium and the vocal fold scar was categorized as isolated lamina propria loss with intact epithelial layer.

Subject 2 was a 47 years old male who had onset of dysphonia six years prior to enrollment in this study. He was found to have bowing of vocal folds and underwent several collagen injection laryngoplasties without improvement. Additional therapies included anti-reflux regimen and voice therapy. Videostroboscopic exam at enrollment revealed grade 1 mucosal waves on the left and grade 2 mucosal waves on the right vocal fold and incomplete glottic closure. There were no defects on the epithelium and the vocal fold scar was categorized as isolated lamina propria loss with intact epithelial layer.

Subject 3 was a 66 years old female who had onset of dysphonia after being assaulted to the neck area 39 years prior to enrollment in this study. She then developed supraglottic squamous cell carcinoma 33 years prior to enrollment and was treated with external beam radiation therapy. She further suffered from right vocal fold paralysis after a carotid endarterectomy 13 years prior to enrollment. Prior therapies for her voice disorder included anti-reflux regimen, voice therapy, injection laryngoplasty with collagen, and fat injection. Videostroboscopic exam at enrollment revealed grade 1 mucosal waves bilaterally and incomplete glottic closure. The epithelium appeared scarred and bilaterally and the vocal fold scar was categorized as full thickness scar of the vocal fold involving both the lamina propria and epithelial layers.

Subject 4 was a 62 years old male who underwent direct laryngoscopy with excision of right vocal fold nodule 30 years prior to enrollment in this study with resultant long-term dysphonia after surgery. Prior therapies for his voice disorder included multiple collagen injection larygoplasties 3 to 7 years prior to enrollment. Four years prior to enrollment he had superficial collagen injection removed under direct laryngoscopy and three years prior he had bilateral type 1 thyroplasties with silastic implants performed. Videostroboscopic exam at enrollment revealed a right vocal fold sulcus (linear defect on the vocal fold surface throughout the length of the membranous vocal fold) with grade 1 mucosal wave, and an intact left vocal fold with grade 4 mucosal waves. The vocal fold scar was categorized as unilateral sulcus type. Subject 4 was the only enrollee to receive unilateral vocal fold treatment in this study.

Subject 5 was a 68 years old female who underwent laser ablation of Reinke's edema four years prior to enrollment. Her dysphonia ensued. Subsequent treatments included three separate treatments with fat injections. She responded to the first two injections but not to the third. Six months prior to enrollment she underwent injection laryngoplasty with calcium hydroxylapatite. She continued to be severely dysphonic. Videostroboscopic exam at enrollment revealed grade 1 mucosal waves bilaterally. The epithelium appeared scarred bilaterally and the vocal fold scar was categorized as full thickness scar of the vocal fold involving both the lamina propria and epithelial layers.

Buccal Biopsy and Cellular Expansion:

All five subjects underwent buccal mucosal biopsy without complications and all biopsy sites rapidly healed by secondary intention. An average of 122 days (range 63-196 days) was required from biopsy to treatment. One patient required a second biopsy due to bacterial contamination detected late in the fibroblast expansion process. Cell expansion was otherwise unremarkable and cell specifications were reached for all subjects. Cell viability at injection was above specification (>85%) in all subjects (actual range 86%-96%). Cell concentration was within specification (1.0-2.0×10$^7$ cell/mL) in all injections (actual range 1.1 to 2.0×10$^7$ cells/mL). Gram stains were performed in samples from each treatment vial prior to packaging and were negative. An aliquot from each injection vial was also used for culture and no microbiologic contaminants, including mycoplasma, were cultured from the monitored samples. Mycoplasma was tested at the Bulk Harvest stage, not in the final injection. Sterility test was performed for each vial filled, but released using Gram stain. The sterility test was not finalized until after injection.

Safety Endpoints:

All five subjects received study treatment of 1-2×10$^7$ cells/mL. Each scarred vocal fold received three treatments at four week intervals. One subject (Subject 4) had unilateral vocal fold scarring and received a total of three injections. The other four subjects had bilateral vocal fold scarring and received a total of six injections each. Thus patients with bilateral vocal fold scarring were seen at 2-week intervals whereas only one vocal fold was injected per visit. Of the total 27 treatment injections performed, the full treatment dose of 1.0 ml was injected in 24 instances (89%). In the other three instances 0.85 ml (Subject 1, Treatment #1), 0.5 ml (Subject 5, Treatment #6), and 0.3 ml (Subject 3, Treatment #6) were injected. In the first instance, less than 1.0 mL was injected because a small amount was lost during aspiration of cells from the treatment vial, while in the latter two instances the treatment injections were terminated prematurely due to complaints of severe otalgia during the injection.

Subjects were observed for one hour after each treatment injection. Repeat endoscopy was performed the day after the first treatment. Subjects were contacted by telephone on days 2 through 4 after treatment to check on the airway status and other constitutional symptoms such as fever, chills, neck swelling, or other new symptoms. There were no adverse reactions noted by the investigator or reported by the subjects.

During each treatment and follow-up visits adverse events (AEs) were actively sought and collected. Two subjects experienced a total of 12 AEs considered related to treatment. These were mild to severe otalgia suffered during treatment in subjects 3 and 5. These were subjects categorized as having extensive full thickness vocal fold scars of the cover layer, involving scarring of the epithelial layer as well as lamina propria loss. The otalgia was considered definitely related to study treatment as it was experienced by these subjects as they were receiving the injection treatment, and the pain symptoms correlated temporally with the moment the cells being injected in the lamina propria compartment were dissecting the epithelial layer off from the muscle layer. The otalgia was mild to moderate in 10 instances and severe in 2 instances. As mentioned earlier, in the latter two instances the treatment was terminated prematurely prior to injection of the full 1.0 mL dose. The otalgia resolved rapidly after the injection was terminated and was absent by the time of discharge from the clinic. The other three subjects had no otalgia complaints. There were no deaths or serious adverse events. No subject was discontinued from the study due to AEs.

Laboratory assessments were analyzed by flagging each laboratory value low (L), high (H), and normal (N) based on the investigational site lab normal range. The percentage change from baseline was also calculated and the Wilcoxon Signed-Rank test was used to determine if a statistically significant change from baseline was present. There were no clinically significant changes in laboratory parameters. In fact all the laboratory parameters were within normal in all subjects at all assessment time periods. There were no clinically significant changes in vital signs (respiration rate, heart rate, temperature, and blood pressure) from baseline during the course of the study (Wilcoxon Signed-Rank Test).

Primary Efficacy Endpoint:

Mucosal Wave Grade:

The primary efficacy endpoint assessed in this study was the change from baseline in mucosal wave grade using videostroboscopy of each treated vocal fold. Table 1 lists each subject by scar type and provides mucosal wave grade for each subject at various assessment intervals. Note that not all five subjects completed the assessment for each visit and all values were calculated based on non-missing values. A positive change in mucosal wave grade from baseline indicated improvement. The mean change from baseline in mucosal wave grade showed improvement at week 8, and significantly at months 3, 4, and 12. This demonstrates sustained improvement in mucosal wave starting at week eight and continuing up to the end of the study assessment at month 12.

A closer review of the mucosal wave data reveals that the two subjects with the isolated lamina propria loss (Subjects 1 and 2) and the subject with sulcus scar (Subject 4) improved most with treatment. The two subjects with full thickness cover scarring (Subjects 3 and 5) had essentially no improvement; subject 3 had no improvement in mucosal grade at all assessment time intervals, and subject 5 continued to have severe scarring throughout the study period (mucosal wave grade 1-2) until the 12 month interval assessment when the left vocal fold appeared to have slightly improved mucosal wave (mucosal wave grade 3).

Review of videostroboscopic recording in subject 4 revealed that although the mucosal waves improved, the physical appearance of the sulcus (linear defect on the vocal fold surface) remained unchanged throughout the study period. Lower scores indicate improved perception of the impact of the voice disorder by the subject. The total score is given followed by the change (in parenthesis) compared to baseline VHI score at day 0. A change of 18 points from Day 0 is considered significantly different (bolded).

TABLE I

Demographic, Past Vocal History, and Laryngoscopic Findings

| Subject No/Sex/Age | Etiology or Associated Disorders | Duration | Failed Prior Rx | MW grade Right | MW grade Left | Status of Epithelium | Glottic Gap |
|---|---|---|---|---|---|---|---|
| 1/35/M | Tonsillectomy GERD | 5 years | PPI, Voice Rx | 2 | 2 | Intact | Yes |
| 2/47/M | Bowing | 6 years | PPI, Voice Rx, IL | 2 | 1 | Intact | Yes |
| 3/66/F | SCCA/XRT Right VFP | 33 years 13 years | PPI, Voice Rx, IL, Fat Injection | 1 | 1 | Scarred | Yes |
| 4/62/M | Cold MDL for nodule | 30 years | PPI, Voice Rx, IL, Type 1 Thyroplasty | 1 | 4 | Sulcus | Yes |
| 5/68/F | Laser MDL for edema | 4 years | PPI, Voice Rx, IL Fat Injection | 1 | 1 | Scarred | Yes |

GERD = Gastro Esophageal Reflux Disease,
SCCA = Squamous Cell Carcinoma,
XRT = Radiation Therapy,
VFP = Vocal Fold Paralysis,
MDL = Microsuspension Direct Laryngoscopy with excision of lesion,
PPI = Proton Pump Inhibitor,
Voice Rx = Voice Therapy,
IL = Injection Laryngoplasty Secondary Efficacy Endpoints:
Harmonic-to-Noise Ratio:

The change from baseline in Harmonic-to-Noise ratio was examined for all subjects at each assessment. Sounds that are considered noise generally have no harmonic structure. A smaller (or negative) value of Harmonic-to-Noise ratio (dB) indicates more noisy voice signal and thus increased vocal fold pathology. The absolute change from baseline in Harmonic-to-Noise ratio was calculated at each time point by subtracting the Harmonic-to-Noise ratio at each respective assessment from the Harmonic-to-Noise ratio at baseline. These values were tested for statistically significant differences from baseline using the Wilcoxon Signed-Rank test. A positive absolute change from baseline in the Harmonic-to-Noise ratio indicates improved vocal fold pathology.

Table 2 provides summary information for subject assessment for Voice Recording for Acoustic Analysis of Harmonic-to-Noise ratio. These results suggest that most subjects experienced little change from baseline in the voice recording for acoustic analysis of the Harmonic-to-Noise ratio after treatment. A closer examination of the measurements shows a random distribution of this measure and likely means that this measure is not useful in this group of subjects.

TABLE 2

Mucosal Wave Grade at Various Intervals

| Subject | Scar Type | Vocal Fold | Day 0 | Week 4 | Week 8 | Month 3 | Month 4 | Month 8 | Month 12 |
|---|---|---|---|---|---|---|---|---|---|
| 1 | Lamina propria only | Left | 2 | — | 2 | — | 4 | — | 4 |
|   |   | Right | 2 | — | 3 | — | 4 | — | 4 |
| 2 | Lamina propria only | Left | 1 | 1 | 3 | 5 | 4 | — | 5 |
|   |   | Right | 2 | 2 | 4 | 5 | 5 | — | 5 |
| 3 | Lamina propria & epithelium | Left | 1 | 1 | 1 | 1 | 1 | 1 | 1 |
|   |   | Right | 1 | 1 | 1 | 1 | 1 | 1 | 1 |
| 4 | Sulcus | Right | 1 | 2 | 4 | 4 | 4 | 4 | 4 |
| 5 | Lamina propria & epithelium | Left | 1 | 1 | 1 | 2 | 2 | 2 | 3 |
|   |   | Right | 1 | 1 | 1 | 2 | 2 | 2 | 2 |
| Mean Mucosal Wave Grade | | | 1.3 | 1.3 | 2.2 | 2.9 | 3 | 2 | 3.22 |
| Wilcoxon Signed Rank p-value | | | | 0.32 | 0.07 | 0.04 | 0.02 | 0.10 | 0.02 |

Mucosal Wave Grades Prior to and Following Treatment with autologous fibroblasts. Subjects 1, 2, 3, and 5 received six treatments (3 to each vocal fold) starting Day 0 and completing at Week 10 as described in Materials and Methods. Subject 4 received three treatments with starting at Day 0 and completing at Week 8. Mucosal wave grades were assigned by consensus between a laryngologist and an experienced speech pathologist. Missing grades (—) indicate that the test was not performed for that visit. Statistical significance of the change from baseline was assessed with Wilcoxon Signed-Rank test. "Scar Type" indicates the baseline assessment of scar (involvement of lamina propria only or lamina propria and epithelium).

Maximum Phonation Time:

The change from baseline in Maximum Phonation Time was examined for all subjects at each assessment. A longer phonation time (sec) indicates an improved respiratory and laryngeal sound control. The absolute change from baseline in the Maximum Phonation Time was calculated at each time point by subtracting the baseline Maximum Phonation Time from the Maximum Phonation Time at each respective assessment. These values were tested for statistically significant differences from baseline using the Wilcoxon Signed-Rank test. A positive absolute change from baseline in the Maximum Phonation Time indicates improved vocal fold pathology.

Table 3 provides summary information for acoustic analysis of Maximum Phonation Time. Table 3 shows improvement from baseline beginning at the Week 8 visit with a median change of 1.0. At Months 3 and 4, the Maximum Phonation Time showed further improvement, with median changes of 4.0 and 2.3, respectively. However, by Month 8 there was a worsening from baseline and at Month 12 only a minimal improvement from baseline was seen. These results suggest a trend for improvement in vocal fold pathology at Months 3-4 that is not sustained.

TABLE 3

Voice Handicap Index VHI) Scores at Various Time Intervals by Subject

| Subject | Day 0 | Week 4 | Week 8 | Month 3 | Month 4 | Month 8 | Month 12 |
|---|---|---|---|---|---|---|---|
| 1 | 101 | 68 (−33) | 75 (−26) |  | 56 (−45) |  | 56 (−45) |
| 2 | 82 | 79 (−3) | 84 (+2) | 66 (−16) | 69 (−13) | 67 (−15) | 55 (−27) |
| 3 | 79 | 75 (−4) | 52 (−27) | 55 (−24) | 50 (−29) | 51 (−28) | 50 (−29) |
| 4 | 68 | 62 (−6) | 41 (−27) | 36 (−32) | 41 (−27) | 34 (−34) | 30 (−38) |
| 5 | 89 | 98 (+9) | 77 (−12) | 79 (−10) | 63 (−26) | 58 (−31) | 72 (−17) |
| Total with significant change |  | 1/5 | 3/5 | 2/4 | 4/5 | 3/4 | 4/5 |

Voice Handicap Index (VHI):

Assessment of the VHI consisted of testing the absolute and percentage change from baseline at each follow-up assessment. The VHI scores were calculated for each of the three subscales and the overall total. Each of these was tested for differences from baseline. Additionally, the percentage change from baseline in VHI was calculated by subtracting the score at the respective assessment from the score at baseline and dividing that difference by the baseline score and multiplying by 100%. These values were tested for statistically significant differences from baseline using the Wilcoxon Signed-Rank test.

Figure 3:
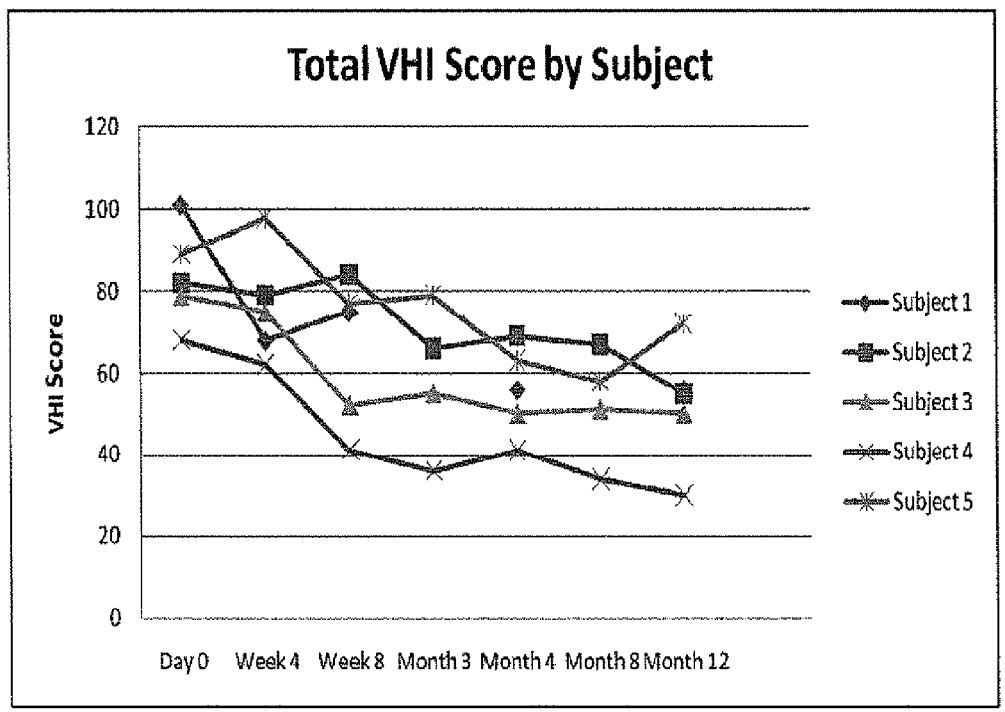
FIG. 3 is a graph of VHI score over time (in months).

Note that higher VHI scores indicate a more severe perception of the impact of the voice problem. The absolute change from baseline was calculated by subtracting the score at the respective assessment from the score at baseline. Each subscale has been found to be significantly different if it differed by eight points, whereas the total VHI score has been found to be significantly different if it differs by 18 points (21). FIG. 3 illustrates that most of the change in overall VHI score occurred between weeks 8 and month 3 and that the change was maintained for the rest of the study period.

Subject assessment for VHI—Part 1 (Functional) shows a positive absolute change, which indicates improvement, beginning at the Week 4 visit and sustained through the Month 12 visit. Similar changes were indicated in the percentage change from baseline. These results suggest a trend for improvement in the VHI—Part 1 (Functional) that is sustained through Month 12.

Subject assessment for VHI—Part 2 (Physical) showed similar results for the VHI—Part 2 (Physical) as for the VHI—Part 1 (Functional). Sustained improvement from baseline was seen at Week 4 through Month 12.

The VHI—Part 3 (Emotional) showed similar results to both VHI—Part 1 and 2. An improvement from baseline was seen at Week 8 that was sustained through Month 12.

The VHI-Overall showed the same results as the VHI subparts. Improvements from baseline were seen at all study visits. These results suggest a trend for acute improvement that is sustained through 12 months.

Subject's VAS Assessment of Vocal Fold Improvement:

The subject was asked to rate the vocal fold improvement using a VAS at Week 4, Week 8, and during all follow-up visits. The VAS ranged from "Worst Possible Change from Baseline" (score of −50) on the left side to "Most Possible Improvement from Baseline" (score of 50) on the right side. Thus the VAS at each assessment was measured and given a score from −50 to 50. These values were tested for statistically significant differences from baseline using the Wilcoxon Signed-Rank test. A positive value indicates improvement.

Subject's VAS Assessment of Vocal Fold Improvement shows, beginning at Week 8 subjects indicated improvement from baseline with a median change of 17.0. At Months 3, 4, 8, and 12, subjects continued to indicate improvement with median changes of 22.0, 18.0, 17.5, and 30.0 respectively. At Month 4 one subject (subject #4) entered a negative VAS (score −28) and yet answered "improved" to the question "Has your voice changed since baseline" and "Yes" to the question "Do you consider the treatment a success?", thus affecting the p-value significance trend at Month 4. Nevertheless, these results suggest a trend for improvement in the VAS Assessment for Vocal Fold Improvement that is sustained through Month 12.

Subject's Impression of Voice Quality Questionnaire:

At each assessment, the proportion of subjects that reported each response was tabulated, and 95% confidence intervals calculated. Subject's Impression of Voice Quality Questionnaire for the question "How has your voice quality changed since baseline?" shows that beginning at Week 8, the majority of subjects indicated "Improved" for the question. These results indicate that most subjects considered that their voice quality had improved since baseline, and that this improvement was sustained through the Month 12 visit. Subject's Impression of Voice Quality Questionnaire for the question "Do you consider the treatment a success?" shows that, beginning at Week 8, the majority of subjects indicated that the treatment was a success at each visit, most indicating "YES" for the question. These results indicate that most subjects considered their treatment to be successful, and that this benefit was sustained through Month 12.

Discussion

The results show that autologous fibroblast therapy significantly improves mucosal waves in this cohort. Assessment of the primary efficacy endpoint, the mucosal wave grade, showed an improvement at the week 8 visit that was sustained until the end of the study (Month 12). While the small number of subjects in this Phase I trial limited statistical significance for many secondary measures, a trend towards statistical significance was achieved. The results for analysis of the Voice Handicap Index (all categories) showed sustained improvements from baseline. The Voice Quality Questionnaire showed that the majority of subjects considered that their voice quality had improved, and that this improvement was sustained throughout Month 12. Acute improvement that was not sustained after Month 4 was observed for maximal phonation time. The assessment of Harmonic-to-Noise ratio showed no meaningful changes or trends. In addition, the most important goal, to show that autologous fibroblasts can be harvested and expanded in the laboratory and safely re-injected into the subject, was achieved. The only adverse event related to the study treatment was otalgia during vocal fold injection. It appears that subjects with full thickness scars are more susceptible to otalgia and that in most instances the pain was tolerable enough so that the procedure could be completed and the full treatment dose given.

Another important finding in this study is that subjects with full thickness cover defects had minimal improvement of their mucosal waves although improvement in other measures was noted. It is possible that the stroboscopic measure of mucosal wave grade does not yield information that is obtained with other measures. For example, subjects may have perceived improved efficiency of phonation, or there may have been improvement in other factors that were not measured in this study that lead to subjects' improved perception of voice. Finally, one must also consider the placebo effect of repeated injections. It appears that the when vocal fold scars are extensive and the regenerated epithelium is also scarred and stiff, replacement of the lamina propria layer alone is unlikely to improve the mucosal wave, which requires a pliable epithelial layer as well. These defects may be better treated with full thickness cover replacement.

I claim:

1. A method for treatment of vocal fold scarring, presbylaryngis and vocal cord augmentation in a human in need thereof comprising injecting into the vocal cord or fold from about 1 ml to 6 ml of the formulation of a dosage formulation comprising between $1.0 \times 10^7$ and $2.7 \times 10^7$ cells/mL, wherein at least 98% of the cells are autologous human fibroblast cells or precursors thereof reactive with a cell surface marker for fibroblasts and not with a cell surface marker for keratinocyte cells, at least 85% of which are viable after freezing and thawing.

2. The method of claim 1 wherein between one and two ml of the cells is injected.

3. The method of claim 1 wherein the cells are layered in the vocal fold subepithelial layer.

4. The method of claim 1 further comprising providing local anesthetic to the nasal cavity or larynx.

5. The method of claim 1 further comprising visualizing the site of injection using a fiberoptic laryngoscope connected to a video monitor.

6. The method of claim 1 further comprising obtaining fibroblast cells from the buccal mucosa of a human and culturing and purifying the cells prior to administration.

7. The method of claim 3 wherein one, two, three or four treatment doses of $1\text{-}2 \times 10^7$ cells/mL are injected into the subepithelial layer of each vocal fold.

8. The method of claim 7 wherein the doses are administered one to eight weeks apart.

9. The method of claim 1 further comprising thawing the cells from frozen prior to washing and concentration to $1\text{-}2 \times 10^7$ cells/ml.

* * * * *